United States Patent [19]

Olson et al.

[11] Patent Number: 5,797,969
[45] Date of Patent: Aug. 25, 1998

[54] ONE BUTTON LID ACTIVATED AUTOMATIC EXTERNAL DEFIBRILLATOR

[75] Inventors: Kenneth F. Olson, Minneapolis; Byron L. Gilman, Plymouth; Katherine H. Anderson, Golden Valley, all of Minn.

[73] Assignee: SurVivaLink Corporation, Minneapolis, Minn.

[21] Appl. No.: 781,185

[22] Filed: Jan. 9, 1997

Related U.S. Application Data

[63] Continuation of Ser. No. 512,441, Aug. 8, 1995, Pat. No. 5,645,571, which is a continuation-in-part of Ser. No. 509,990, Aug. 1, 1995, abandoned.

[51] Int. Cl.$^6$ .................................................... A61N 1/39
[52] U.S. Cl. .................................................... 607/5
[58] Field of Search .................................. 607/5, 142

[56] References Cited

U.S. PATENT DOCUMENTS

| | | |
|---|---|---|
| 3,857,398 | 12/1974 | Rubin . |
| 3,886,950 | 6/1975 | Ukkestad et al. . |
| 4,077,413 | 3/1978 | Partridge .................. 607/5 |
| 4,494,552 | 1/1985 | Heath . |
| 4,610,254 | 9/1986 | Morgan et al. . |
| 4,619,265 | 10/1986 | Morgan et al. . |
| 4,823,796 | 4/1989 | Benson . |
| 5,097,830 | 3/1992 | Eikefjord et al. . |
| 5,224,475 | 7/1993 | Berg et al. . |
| 5,249,573 | 10/1993 | Fincke et al. . |
| 5,330,526 | 7/1994 | Fincke et al. . |
| 5,402,884 | 4/1995 | Gilman et al. . |
| 5,405,361 | 4/1995 | Persson . |
| 5,462,157 | 10/1995 | Freeman et al. ............ 128/640 |
| 5,470,343 | 11/1995 | Fincke et al. . |
| 5,591,213 | 1/1997 | Morgan ..................... 607/5 |
| 5,611,815 | 3/1997 | Cole et al. ................. 607/5 |

FOREIGN PATENT DOCUMENTS

| | | |
|---|---|---|
| 0 487 776 A1 | 11/1990 | European Pat. Off. . |
| WO 94/26350 | 11/1994 | WIPO . |
| WO 94/27674 | 12/1994 | WIPO . |
| WO 95/05215 | 2/1995 | WIPO . |

OTHER PUBLICATIONS

SurVivaLink Corporation Progress Report, Nov. 1, 1993.
"Responder 1500 Defibrillator," Marquette Electronics, undated, 2 pages.
"Lifepak 10," Physio–Control, undated, 2 pages.
"Laedal's Heartstart 3000 ATS," Laerdal Medical Corporation, 1 page, 1991.
"First Medic 510 Defibrillator," SpaceLabs Medical, 1 page, undated.
"First Medic 610 Defibrillator," SpaceLabs Medical, 1 page, undated.
"The Nihon Kohden TEC–7300A Defibrillator," Technical Data, 1 page, undated.
"TEC–7000A Series Portable Defibrillators," 2 pages, undated.
"HP 43110A Defibrillator with EMS Option E01," Hewlett Packard, 2 pages, undated.
"CodeMaster XL,"CodeMaster XE, Code Master XL+, HP CodeMaster XL + Defibrillator, 3 pages, undated.
"Porta–Fib LPD I and LPD IIS," Telecare, 1 page, undated.
"HP 43130A," 1 page, undated.
"Cardiac Emergencies, PPG Hellige Defiport SCP 912," 1 page, undated.
"Zoll Cardiac Resuscitation," Zoll Medical Corporation, 1 page, undated.

(List continued on next page.)

*Primary Examiner*—William E. Kamm
*Assistant Examiner*—Carl H. Layno
*Attorney, Agent, or Firm*—Patterson & Keough, P.A.

[57] ABSTRACT

An automated external defibrillator which automatically performs self-tests on a daily and weekly basis. Tested functions include the presence and interconnection of defibrillator electrodes, battery charge state and the operability of the high voltage circuit. Visual and audible indicators are actuated to alert an operator if faults are identified. A record of each self-test is stored in memory, and can be subsequently retrieved through a communications port.

19 Claims, 4 Drawing Sheets

OTHER PUBLICATIONS

"Zoll PD 1400 Pacemaker/Defibrillator," Zoll Medical Corporation, 1 page, undated.

"First Medic 610 Semi–Automatic Defibrillator," 1 page, undated.

"Lifepak 11 diagnostic cardiac monitor," Physio Control, 1 page, undated.

"Lifepak 10 defibrillator/monitor/pacemaker," Physio Control, 1 page, undated.

"Lifepak 250 automatic advisory defibrillator," Physio Control, 1 page, undated.

"Proof that good things come in small packages," 1 page, undated.

"The Tough Team," SpaceLabs, Inc., Feb. 1992, 9 pages.

"Responder 1200 Defibrillator," Marquette Electronics, 1991, 6 pages.

"Laerdal Heartstart 1000s," Laerdal, 9 pages, undated.

"Lifepak 300 automatic advisory defirbrillator without printer," Physio Control, 1 page, undated.

W.A. Tacker, Jr., *Defibrillation of the Heart* 1994 pp. 196–222 (Chapter 10).

"Zoll PD 1400 Pacemaker/Defibrillator," Zoll Medical Corporation, 1 page, Physio Control Lifepak 300 Operating Instructions 40 pp.

Laerdal Medical, Laerdal Heartstart 2000 Operating Instructions 17 pp.

"First Medic 510 Semi–Automatic Defibrillator," 4 pp.

"First Medic 610 Semi–Automatic Defibrillator," 2 pp.

"First Medic Manager V. 2.0," 1 p.

"Space Labs Medical Operations Manual," 90526 First Medic 610 Semi–Automatic Defibrillator, 37 pp.

"Lifepak® 300 Automatic Advisory Defibrillator—Operating Instructions", Physio–Control, 1990 (p. 7) pp. 1–10.

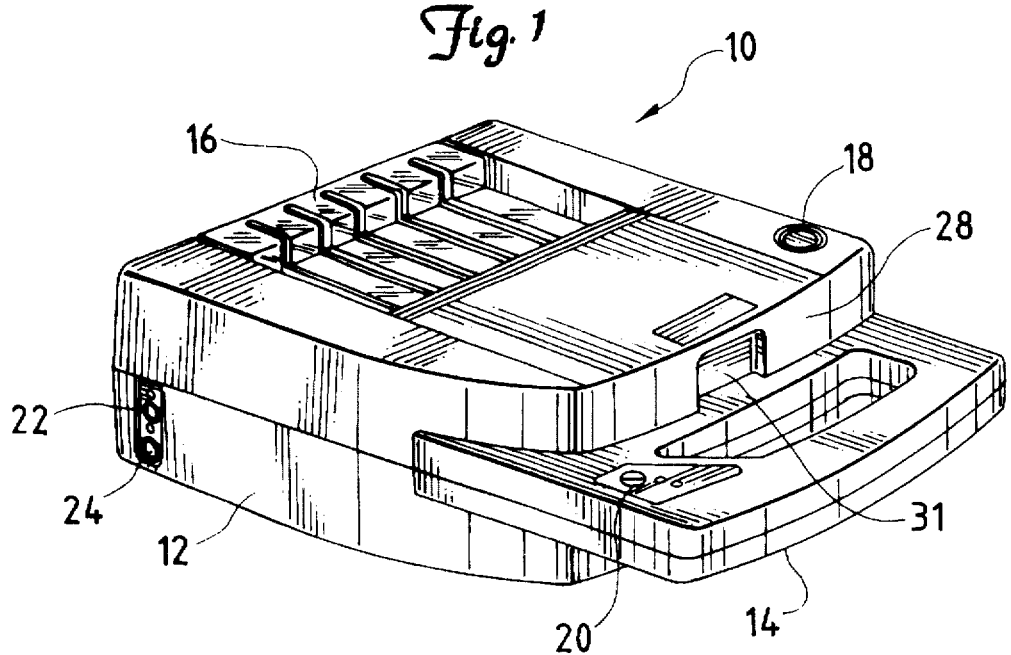
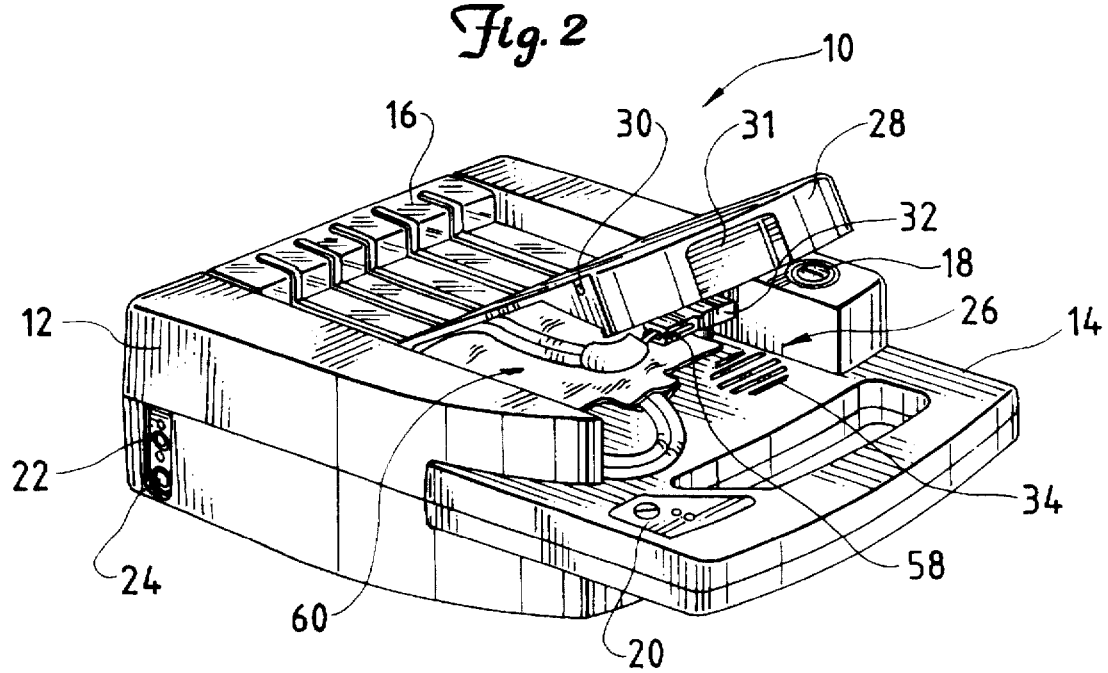

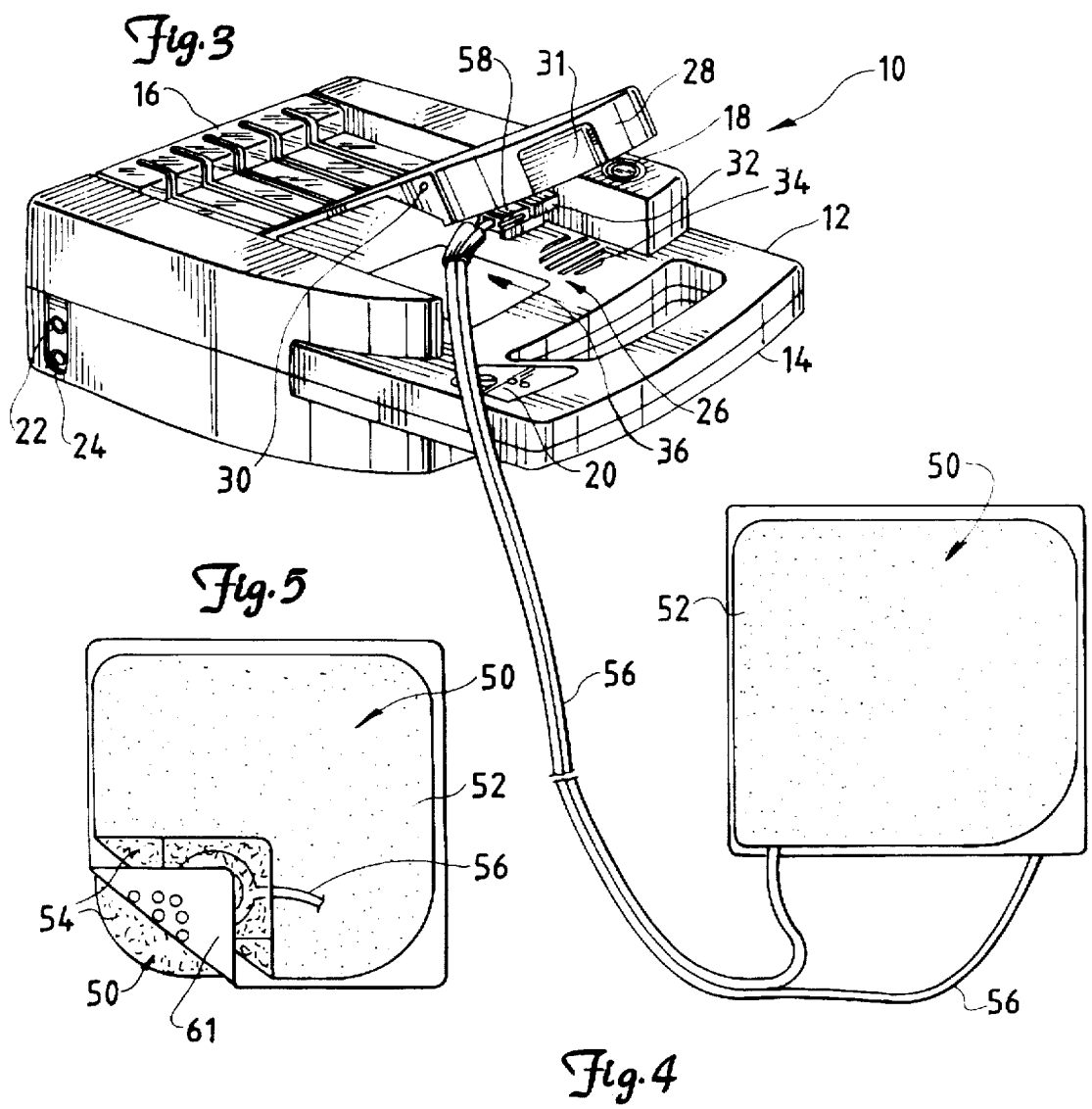
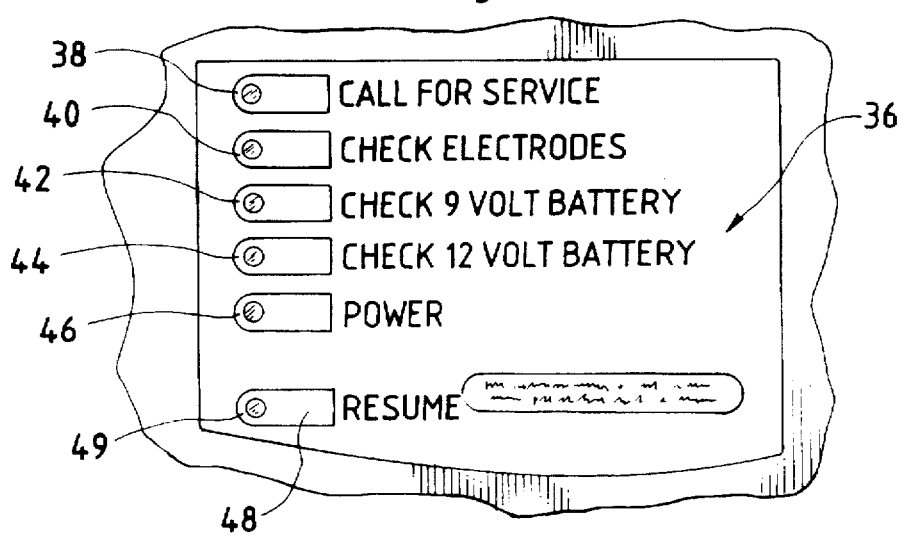

ONE BUTTON LID ACTIVATED AUTOMATIC EXTERNAL DEFIBRILLATOR

REFERENCE TO RELATED APPLICATION

This application is a Continuation of application Ser. No. 08/512,441 filed Aug. 8, 1995, now U.S. Pat. No. 5,645,571 which is a Continuation-In-Part of commonly assigned U.S. application Ser. No. 08/509,990 filed Aug. 1, 1995 which was abandoned on Nov. 11, 1997 and was entitled 'Automated External Defibrillator Operator Interface'.

BACKGROUND OF THE INVENTION

1. Field of the Invention

The present invention relates generally to automated external defibrillators. In particular, the present invention is an automated external defibrillator with a self-test system for automatically and periodically testing the operational status of the defibrillator, and for providing service alerts if faults are identified.

2. Description of the Related Art

Automated external defibrillators or AEDs are used by police officers, paramedics and other first-responder emergency medical technicians to resuscitate cardiac arrest patients. It is important that the AEDs carried by these technicians be continuously operational and ready for use on a moments notice. To help ensure a high level of confidence that they will be operational when needed, AEDs should be periodically checked and tested by the technicians, and corrective maintenance performed if any faults are identified. By way of example, AED functions and components that should be periodically checked and tested include the charge state of the batteries, the presence of electrodes and the ability of the device to charge and deliver defibrillation pulses. The American Heart Association recommends that AEDs be tested daily or at the beginning of a shift.

Unfortunately, for a variety of reasons the frequency at which AEDs are tested by the technicians that will be using them varies. Since studies have shown that the chances of successfully resuscitating a patient decrease approximately ten percent per minute following cardiac arrest, the consequences of first-responder medical technicians arriving at a rescue location with a nonfunctional AED can be severe. There is, therefore, a continuing need for AEDs capable of being reliably maintained in a functional state.

SUMMARY OF THE INVENTION

The present invention is an improved automated external defibrillator (AED). One embodiment of the defibrillator includes a digital control system with self-test means for periodically and automatically performing self-tests of one or more defibrillator components. If a malfunctioning component is identified, the self-test means actuates an audible alarm or other maintenance indicator to alert an operator. Tested functions include the presence and interconnection of defibrillator electrodes, battery charge state, the functionality of the high voltage circuit and the functionality of the digital control system. Some functions are self-tested daily, while others are self-tested weekly.

BRIEF DESCRIPTION OF THE DRAWINGS

FIG. 1 is a perspective view of an automated external defibrillator (AED) in accordance with the present invention, with the electrode compartment lid closed.

FIG. 2 is a perspective view of the AED shown in FIG. 1, with the electrode compartment lid opened and the packaged electrodes positioned therein.

FIG. 3 is a perspective view of the AED shown in FIG. 2, with the electrodes removed from the electrode compartment and the package.

FIG. 4 is a detailed view of the diagnostic display panel in the electrode compartment.

FIG. 5 is a detailed view of the unpackaged electrodes positioned on the release liner.

DETAILED DESCRIPTION OF THE PREFERRED EMBODIMENTS

Figure 6:
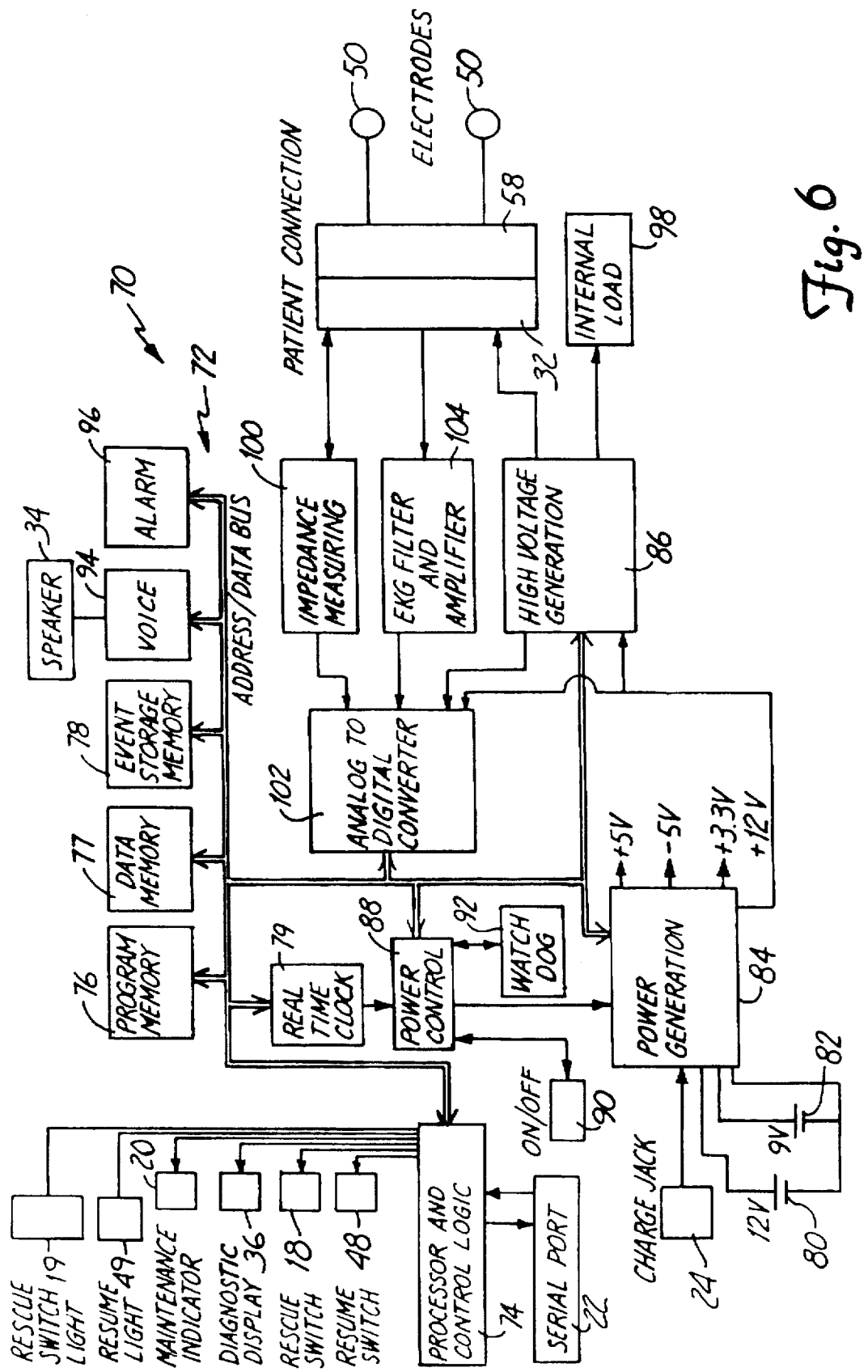
FIG. 6 is a block diagram of the electrical system of the AED shown in FIG. 1.

A semi-automatic, automated external defibrillator (AED) 10 in accordance with the present invention is illustrated generally in FIGS. 1–3. As shown, defibrillator 10 includes a plastic case 12 with a carrying handle 14 on the top portion. A battery compartment (not visible) in the bottom portion of the defibrillator 10 is enclosed by a semi-transparent battery cover 16. An illuminatable rescue switch 18, visual maintenance indicator 20, data communication port 22 and charging port 24 are located on the outside of case 12 for easy access by an operator.

Figure 7:
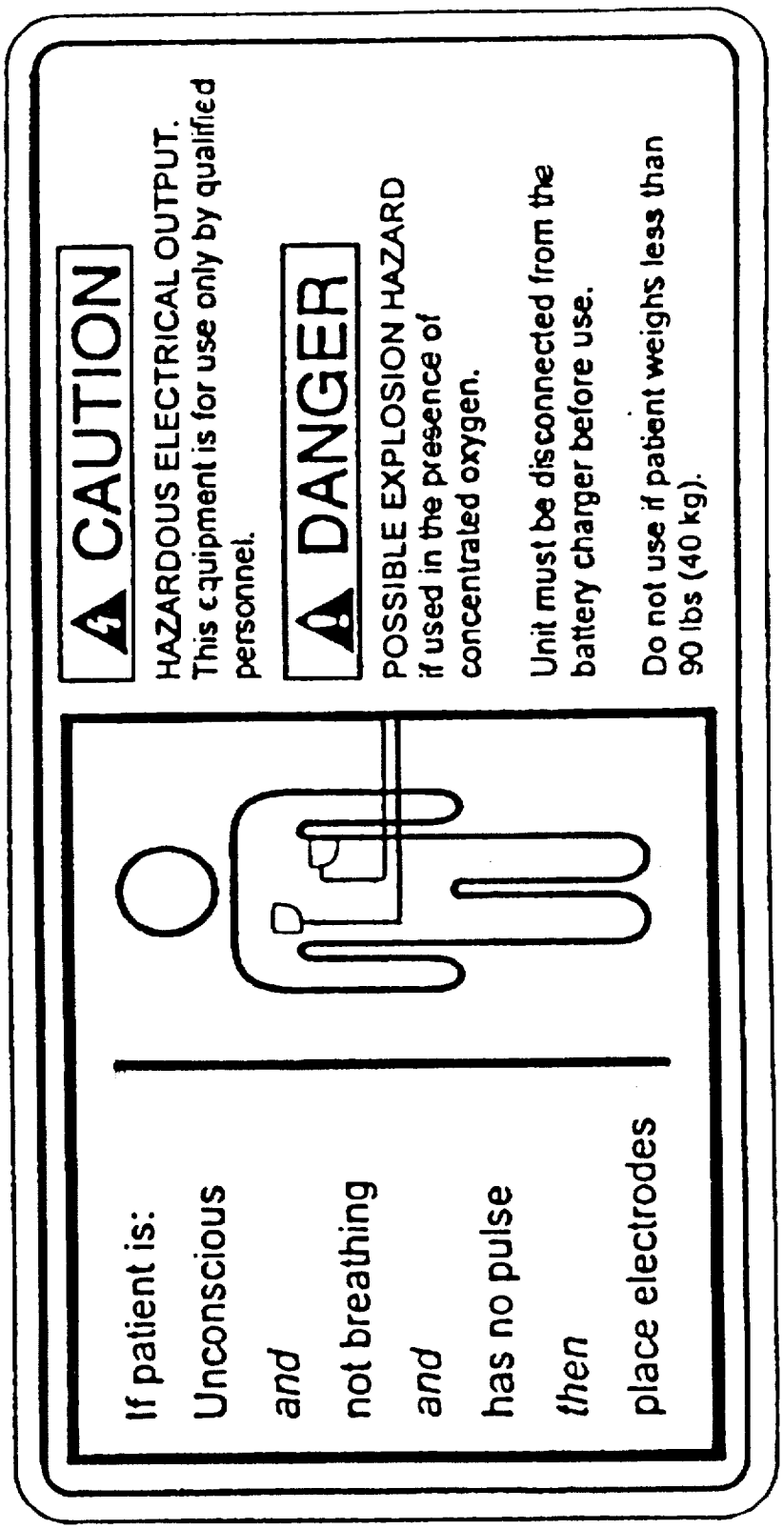
FIG. 7 is an illustration of the instruction and safety label on the inside surface of the electrode compartment lid.

Case 12 also includes an electrode compartment 26 between handle 14 and battery cover 16. The electrode compartment 26 is enclosed by lid 28 which is mounted to the case 12 by hinges (not visible). A friction-type releasable latch including pins 30 holds lid 28 closed when defibrillator 10 is not in use. The finger-receiving recess 31 in the lid 28 is grasped to open the lid and access the electrode compartment 26. An electrode connector 32, speaker 34 and diagnostic display panel 36 are located on case 12 within the electrode compartment 26. As shown in FIG. 4, diagnostic display panel 36 includes visual "Call for Service" indicator light 38, "Check Electrode" indicator light 40, "Check 9 Volt Battery" indicator light 42, "Check 12 Volt Battery" indicator light 44 and "Power" indicator light 46. Resume switch 48 and resume indicator light 49 are also located on diagnostic panel 36. An instruction and safety label such as that shown in FIG. 7 is located on the inside surface of electrode compartment lid 28.

A pair of defibrillator electrodes 50 which can be used with defibrillator 10 are shown in FIGS. 3 and 5. Electrodes 50 each include a flexible polymer backing layer 52 and a patient-engaging layer 54 of conductive adhesive which overlays the backing layer. A current-dispersing flexible conductive sheet (not visible) is located between the backing layer 52 and patient-engaging layer 54. Insulated lead wires 56 extend from each electrode 50, and have a first end connected to the conductive sheet and a second end connected to connector 58. Connector 58 is configured to releasably mate with the electrode connector 32 in electrode compartment 26. Electrodes 50 are sealed within a polymer or polymer-metal laminate package 60 such as that shown in FIG. 2. Lead wires 56 and connector 58 extend from package 60. The layers 54 of electrodes 50 are affixed in a face-to-face orientation to opposite sides of a release liner 61 within package 60. The release liner 61 is perforated with a number of apertures, so the electrodes 50 are electrically coupled to one another within the package 60. A relatively low resistance electrical circuit is thereby established between the ends of the lead wires 56 at connector 58. As shown in FIG. 2, electrode package 60 is positioned within electrode compartment 26, and connector 58 plugged into the connector 32 in the compartment, to maintain defibrillator 10 in a ready-to-use state. Packaged electrodes 50 having the above-described characteristics are disclosed in the Gilman et al. U.S. Pat. No. 5,402,884, and are commercially available from Survivalink of Minnetonka, Minnesota.

FIG. 6 is a block diagram of the electrical system 70 of defibrillator 10. The overall operation of defibrillator 10 is controlled by a digital microprocessor-based control system 72 which includes a processor 74 interfaced to program memory 76, data memory 77, event memory 78 and real time clock 79. The operating program executed by processor 74 is stored in program memory 76. Data memory 77 is used by processor 74 as a scratch pad memory during the execution of the operating program. Electrical power is provided by a rechargeable twelve volt lead-acid cartridge battery 80 and a nine volt battery 82 which are removably positioned within the battery compartment and connected to power generation circuit 84. During normal operation, power generation circuit 84 generates regulated ±5 V, 3.3 V and 12 V (actually about 13.3 V) supplies with the power provided by the twelve volt battery 80. Nine volt battery 82 functions as a back-up battery to power components of electrical system 70 during the execution of self-tests and to activate maintenance indicators and alarms (as described below) if the twelve volt battery 80 is low on charge. Although not separately shown in FIG. 6, power generation circuit 84 includes voltage level sensing circuits which are coupled to processor 74. The voltage level sensing circuits provide low battery level signals to processor 74 whenever the voltage levels of batteries 80 or 82 are less than predetermined values such as 12.3 V and 8 V, respectively.

The ±5 V supply is used to power the control system 72 and most other electrical components of electrical system 70. The 3.3 V supply is coupled to nonvolatile event memory 78 in which, as is described in greater detail below, data representative of the patient's cardiac rhythm and the rescue mode operation of defibrillator 10 are stored. A high voltage generation circuit 86 is connected to receive the 12 V supply. Charging port 24 is coupled to power generation circuit 84, enabling twelve volt battery 80 to be connected to a twelve volt vehicle battery (not shown) or a 120 VAC charger (also not shown) and recharged while mounted within the defibrillator 12. Alternatively battery 80 can be removed from defibrillator 10 and charged in a stand-alone charger (not shown). Defibrillator 10 cannot be operated when a charger is connected to charge port 24. Circuitry (not separately shown) within power generation circuit 84 senses the interconnection of port 24 to a charger, and provides a charger connected signal to processor 74 when a connected charger is sensed.

Power generation circuit 84 is also connected to power control circuit 88 and processor 74. Power control circuit 88 is connected to lid switch 90, watch dog timer 92, real time clock 79 and processor 74. Lid switch 90 is a magnetic reed relay switch in one embodiment, and provides signals to processor 74 indicating whether lid 28 is open or closed. Data communication port 22 is coupled to processor 74 for two-way serial data transfer using an RS-232 protocol. Rescue switch 18, maintenance indicator 20, rescue switch light 19, resume switch 48, indicator lights 38, 40, 42, 44, 46 and 49 of diagnostic display panel 36, voice circuit 94 and piezoelectric audible alarm 96 are also connected to processor 74. Voice circuit 94 is connected to the speaker 34. In response to voice prompt control signals from processor 74, circuit 94 and speaker 34 generate the audible voice prompts described below.

High voltage generation circuit 86 is also connected to and controlled by processor 74. Circuits such as 86 are generally known, and disclosed, for example, in the commonly assigned Persson et al. U.S. Pat. No. 5,405,361, which is hereby incorporated by reference. In response to charge control signals provided by the processor 74, high voltage generation circuit 86 is operated in a charge mode during which one set of semiconductor switches (not separately shown) cause a plurality of capacitors (also not shown), to be charged in parallel to the 12 V potential supplied by power generation circuit 84. Once charged, and in response to discharge control signals provided by processor 74, high voltage generation circuit 86 is operated in a discharge mode during which the capacitors are discharged in series by another set of semiconductor switches (not separately shown) to produce the high voltage defibrillation pulses. The defibrillation pulses are applied to the patient through electrode connector 32 which is connected to the high voltage generation circuit 86. Under certain circumstances described below, processor 74 causes high voltage generation circuit 86 to be discharged through an internal resistive load 98 rather than connector 32.

Impedance measuring circuit 100 is connected to electrode connector 32 and real time clock 79, and is interfaced to processor 74 through analog-to-digital (A/D) converter 102. The impedance measuring circuit 100 receives a clock signal having a predetermined magnitude from clock 79, and applies the signal to electrodes 50 through connector 32. The magnitude of the clock signal received back from the electrodes 50 through connector 32 is monitored by impedance measuring circuit 100. An impedance signal representative of the impedance present across electrode connector 32 is then generated by circuit 100 as a function of the ratio of the magnitudes of the applied and received clock signals (i.e., the attenuation of the applied signal). For example, if the electrodes 50 within package 60 are operational and the connector 58 is properly connected to connector 32 on defibrillator 10, a relatively low resistance (e.g., less than about ten ohms) should be present across the connector 32. If the conductive adhesive on the electrodes 50 is dried out, the connector 58 is not properly connected to connector 32, or the electrodes are not properly positioned on the patient, a relatively high resistance (e.g. greater than about one hundred ohms) will be present across the connector 32. The resistance across connector 32 will be between about fifty and eighty ohms when fresh electrodes 50 are properly positioned on the patient with good electrical contacts. The impedance signal representative of the impedance measured by circuit 100 is digitized by A/D converter 102 and provided to processor 74.

Defibrillator 10 also includes electrocardiogram (EKG) filter and amplifier 104 which is connected between electrode connector 32 and A/D converter 102. The EKG or cardiac rhythm of the patient is processed by filter and amplifier 104 in a conventional manner, and digitized by A/D converter 102 before being coupled to processor 74.

The rescue mode operation of defibrillator 10 is initiated when an operator opens lid 28 to access the electrode package 60. The opening of the lid 28 is detected by lid switch 90, which effectively functions as an on/off switch. In response to this action, power control circuit 88 activates power generation circuit 84 and initiates rescue mode operation of processor 74. Processor 74 then begins its rescue mode operation by switching maintenance indicator 20 to a maintenance required state (e.g., a yellow visual display in one embodiment), flashing rescue switch light 19 and the indicator lights on diagnostic display panel 36, and performing a lid opened self-test. Processor 74 also initiates the generation of an audible voice prompt "To attempt a rescue, disconnect charger." if a charger is connected to charge port 24 when lid 28 is opened.

During the lid opened self-test, processor 74 checks: 1) the charge state of batteries 80 and 82, 2) the interconnection and operability of electrodes 50, 3) the state of event memory 78, 4) the functionality of real time clock 79, and 5) the functionality of A/D converter 102. The charge states of batteries 80 and 82 are checked by monitoring the voltage level signals provided by power generation circuit 84. If batteries 80 and/or 82 are determined to have a low charge, lights 44 and/or 42, respectively, on diagnostic display panel 36 are illuminated by processor 74. The interconnection and operability of the electrodes 50 is checked by monitoring the impedance signals provided by impedance measuring circuit 100. If the package 60 of electrodes 50 is missing or unplugged from connector 32, or if the electrodes are damaged (e.g., dried out), processor 74 will illuminate the indicator light 40 on diagnostic display panel 36. As described in greater detail below, data representative of the operation of defibrillator 10 during a rescue and the patient's cardiac rhythm are stored in event memory 78. The data can be subsequently retrieved from event memory 78 through communications port 22, and the memory cleared. During the lid opened self-test, processor 74 accesses the event memory 78 to determine whether data from a previous rescue is still stored in the memory. If so, processor 74 causes light 49 on diagnostic panel 36 to be illuminated, and initiates the generation of a "Press resume button to clear memory and continue." voice prompt. If resume switch 18 is pressed by the operator following the activation of these indicators, processor 74 clears event memory 78 and proceeds with its rescue mode operation. The functionality of real time clock 79 and A/D converter 102 are checked by monitoring the outputs of these circuit elements for expected signals. Diagnostic display panel light 38 is illuminated by processor 74 if faults are identified in either of clock 79 or converter 102.

If the lid opened self-test is successfully completed, processor 74 switches maintenance indicator 20 to an operational state (e.g., a black color in one embodiment), and initiates the generation of an audible "Place electrodes." voice prompt. In response to this voice prompt, and following the instructions on the inside of lid 28, the operator should remove electrode package 60 from compartment 26, open the package, peel electrodes 50 from the release liner 61 and place the electrodes on the patient's chest. While this action is being performed, processor 74 monitors the impedance signals received through A/D converter 102 to determine whether the impedance across the electrodes indicates that they have been properly positioned on the patient. If the correct impedance is not measured, processor 74 initiates the generation of a "Check electrodes." voice prompt.

After detecting an impedance indicating the proper placement of electrodes 50, and without further action by the operator (i.e., automatically), processor 74 begins a first analyze sequence by initiating the generation of a "Do not touch patient. Analyzing rhythm." voice prompt, and analyzing the patient's cardiac rhythm. In one embodiment, processor 74 collects and analyzes a nine second segment of the patient's cardiac rhythm. The cardiac rhythm analysis program executed by processor 74 is stored in program memory 76. Algorithms of the type implemented by the rhythm analysis program are generally known and disclosed, for example, in the W. A. Tacker Jr. book *Defibrillation of the Heart*, 1994. If the processor 74 determines that the patient has a nonshockable cardiac rhythm that is not susceptible to treatment by defibrillation pulses (e.g., no pulse rather than a fibrillating rhythm), it initiates the generation of a "Check pulse. If no pulse, give CPR." voice prompt. One minute after this voice prompt, processor 74 repeats the initiation of the "Do not touch patient. Analyzing rhythm." voice prompt and the associated cardiac rhythm analysis.

When a shockable cardiac rhythm is detected, processor 74 begins a first charge sequence by initiating the generation of a "Charging." voice prompt, and causes high voltage generation circuit 86 to operate in the charge mode. When the high voltage generation circuit 86 is charged, processor 74 begins a first shock sequence by initiating the generation of a "Stand clear. Push flashing button to rescue." voice prompt, and the flashing illumination of rescue switch light 19. The operator actuation of rescue switch 18 will then cause processor 74 to operate high voltage generation circuit 86 in the discharge mode, and results in the application of a defibrillation pulse to the patient to complete the first series of analyze/charge/shock sequences. In one embodiment, the first defibrillation pulse delivered by defibrillator 10 has an energy content of about two hundred joules.

Following the first series of analyze/charge/shock sequences, processor 74 times out a short pause of about five seconds to allow the heart to reestablish its cardiac rhythm before beginning a second series of analyze/charge/shock sequences. The second series of analyze/charge/shock sequences is identical to the first series described above, except the energy content of the defibrillation pulse can be about two hundred joules or three hundred joules. If the second series of analyze/charge/shock sequences ends with the delivery of a defibrillation pulse, processor 74 again times out a short pause of about five second before beginning a third analyze/charge/shock sequence. The third series is also identical to the first series, but processor 74 controls the high voltage generation circuit 86 in such a manner as to cause the defibrillation pulse delivered upon the actuation of the rescue switch 18 to have an energy content of about three hundred and sixty joules.

Following the delivery of a defibrillation pulse at the end of the third series of analyze/charge/shock sequences, or after identifying a nonshockable cardiac rhythm, processor 74 initiates the generation of a "Check Pulse. If no pulse, give CPR." voice prompt. Processor 74 then times a one minute CPR period to complete a first set of three series of analyze/charge/shock sequences. Rescue mode operation then continues with additional sets of three series of analyze/charge/shock sequences of the type described above (all with three hundred and sixty joule pulses). Processor 74 ends rescue mode operation of defibrillator 10 when a total of nine series of analyze/charge/shock sequences have been performed, or lid 28 is closed.

Throughout the analyze, charge and shock sequences, processor 74 monitors the impedance present across connector 32 to determine whether electrodes 50 remain properly positioned on the patient. If the monitored impedance is out of range (e.g., too high if the electrodes have come off the patient, or too low if shorted), processor 74 initiates the generation of a "Check Electrodes." voice prompt, and causes high voltage generation circuit 86 to discharge any charge that may be present through internal load 98. Rescue mode operation will resume when processor 74 determines that the electrodes have been properly repositioned on the patient.

Processor 74 initiates and performs a lid closed self-test when lid 28 is closed following rescue mode operation of the defibrillator 10. During the lid closed self-test processor 74 performs a comprehensive check of the status and functionality of defibrillator 10, including: 1) the state of event memory 78, 2) the functionality of real time clock 79, 3) the functionality of A/D converter 102, 4) the functionality of program memory 76, data memory 77 and event memory 78, 5) the charge state of batteries 80 and 82, and 6) the interconnection and operability of electrodes 50. The state of event memory 78, the state of batteries 80 and 82, the interconnection and operability of electrodes 50, and the functionality of clock 79 and A/D converter 102 are checked in a manner identical to that described above with reference to the lid opened self-test. Conventional memory test routines are implemented to check the functionality of program memory 76, data memory 77 and event memory 78. Light 38 on diagnostic display panel 36 is illuminated (when lid 28 is subsequently opened), and maintenance indicator 20 is switched to its maintenance required state by processor 74 if faults are identified during the lid closed self-test. No audible alarms are actuated if faults are identified in the charge state of batteries 80 or 82 or the interconnection or functionality of electrodes 50 during the lid closed self test. However, alarm 96 is actuated by processor 74 if other faults are identified during the lid opened self test.

A daily self-test is initiated and performed by processor 74 at a predetermined time each day (i.e., every twenty-four hours). During the daily self-test processor 74 performs all the component check operations described above that are performed during the lid opened and lid closed self-tests. In addition to illuminating the appropriate lights on diagnostic display panel 36, processor 74 switches maintenance indicator 20 to its maintenance required state and activates alarm 96 if faults are identified during the daily self-test.

Processor 74 also initiates and performs a weekly self-test at a predetermined time one day each week. During the weekly self-test processor 74 performs all the component check operations described above that are performed during the daily self-test. In addition, processor 74 causes high voltage generation circuit 86 to sequentially operate in its charge and discharge modes, with the charge being dumped to the internal load 98. While the high voltage generation circuit 86 is operating in the charge mode, processor 74 monitors the time required to charge the capacitors and the capacitor voltage. A fault is identified if either is out of nominal conditions. Maintenance indicator 20 and alarm 96 are actuated in the manner described above if any faults are identified during the weekly self-test.

Watch dog timer 92 is set to time watch dog time-out periods of about thirty hours (i.e., a period greater than the twenty-four hour periods between daily self-tests), and is reset by processor 74 at the beginning of each daily self-test and each time lid 26 is opened. In the event control system 70 malfunctions and watch dog timer 92 times out, power control circuit 88 causes processor 74 to switch maintenance indicator 20 to the maintenance required state and to actuate alarm 96 to alert an operator to the fact that defibrillator 10 requires maintenance.

Data representative of the operation of defibrillator 10 and the monitored cardiac rhythm of the patient are stored in event memory 78 during rescue mode operation. Stored data representative of the operation of defibrillator 10 includes the real time of the occurrence of each of the following events: 1) the placement of electrodes 50 on the patient, 2) the initiation of the cardiac rhythm analysis voice prompt, 3) the initiation of the charging voice prompt, 4) the completion of the charge mode operation of high voltage generation circuit 86, and 5) the actuation of rescue switch 18. The actual time base of the patient's cardiac rhythm is also stored in memory 78. Following a rescue, the stored data can be retrieved from event memory 78 through the use of a personal computer (PC) (not shown) interfaced to communications port 22. Real time clock 79 can also be set through the use of a PC interfaced to communications port 22.

Upon the completion of each lid opened, lid closed, daily and weekly self-test, processor 74 causes a record of the self-test to be stored in event memory 78. Each stored record includes data representative of the date and time of the test and the results of the test. The test results are recorded in the form of a code or other description indicating whether all the functions, components and component status states passed the test, or indicating the nature of any identified faults. In one embodiment, only the records of the ten most recently performed tests are stored in memory 78. The stored self-test records can be retrieved from memory 78 through a PC interfaced to communications port 22.

Defibrillator 10 offers considerable advantages. In particular, the device is relatively easy to use. The lid-actuated on-off switch, voice prompts, "one button" rescue operation and other aspects of the operator interface help enable high-quality defibrillation rescues. The wide range of self-tests and diagnostic displays enable operators to conveniently and accurately assess the operational status of the defibrillator.

Although the present invention has been described with reference to preferred embodiments, those skilled in the art will recognized that changes can be made in form and detail without departing from the spirit and scope of the invention.

What is claimed is:

1. A one button method of applying a defibrillation shock to a patient using an automated external defibrillator (AED) having a case including an electrode compartment, a pair of electrodes stored within the electrode compartment, an openable lid covering the electrode compartment, a high voltage circuit, and an operator-actuated rescue switch, the method including the steps of:

opening the lid covering the electrode compartment to expose the electrodes therein wherein the electrodes are electrically connected to the AED prior to the opening of the lid and wherein the step of opening the lid causes the AED to be powered ON;

retrieving the electrodes stored in the compartment;

applying the electrodes to the patient;

pausing while the high voltage circuit charges; and actuating the operator-actuating rescue switch a single time to apply a defibrillation shock to the patient via the electrodes.

2. The method as in claim 1 further including the step of opening a package containing the electrodes prior to the step of applying the electrodes to the patient.

3. The method as in claim 1 further including the step of peeling the electrodes from a releasable liner prior to the step of applying the electrodes to the patient.

4. The method of claim 1 wherein the step of opening the lid further causes the AED to perform a self-test.

5. An automated external defibrillator (AED) having a case and a lid and a pair of electrodes wherein the AED has a processor for performing initialization and self-checking functions including:

a) monitoring a lid switch;

b) powering ON the AED when the lid switch is activated;

c) initiating a rescue mode when the lid switch is activated;

d) initiating lid opened self-test when the lid switch is activated;

e) initiating a place electrode prompt;

f) monitoring the impedance of the electrodes;

g) initiating a check electrode prompt if the impedance does not fall within a preselected range;

h) beginning a first analyze sequence if the impedance falls within the preselected range;

i) generating a high voltage charge when a shockable rhythm is detected;

j) enabling an operator actuated button for release of a defibrillation shock; and k) initiating a push button to rescue prompt.

6. The defibrillator of claim 5 wherein the rescue mode of function (c) further includes the functions of:

switching a maintenance indicator to a maintenance required stage;

and flashing a rescue light.

7. The defibrillator as in claim 5 wherein the lid open self-test of function (d) further includes the functions of:

checking the charge state of batteries of the AED;

checking the interconnection and operability of the electrodes;

checking the state of a memory in the AED;

checking the functionality of a real time clock of the AED; and checking the functionality of an analog to digital converter of the AED.

8. The defibrillator as in claim 5 wherein functions d, f and j are implemented using an audible voice prompt.

9. The defibrillator as in claim 5 wherein functions d, f and j are implemented using a visual prompt.

10. An automated external defibrillator (AED) having a case and a lid and a pair of electrodes wherein the AED has a processor for performing initialization and self-checking functions including:

a) monitoring a lid switch;

b) powering ON the AED when the lid switch is activated;

c) initiating a rescue mode when the lid switch is activated;

d) monitoring the impedance of the electrodes;

e) beginning a first analyze sequence if the impedance falls within the preselected range;

f) generating a high voltage charge when a shockable rhythm is detected; and g) enabling an operator actuated button for release of a defibrillation shock.

11. The defibrillator of claim 10 wherein the rescue mode of function (c) further includes the functions of:

switching a maintenance indicator to a maintenance required stage; and flashing a rescue light.

12. The defibrillator of claim 10 wherein the lid open self-test of function (d) further includes the functions of:

checking the charge state of batteries of the AED;

checking the interconnection and operability of the electrodes;

checking the state of a memory in the AED;

checking the functionality of a real time clock of the AED; and checking the functionality of an analog to digital converter of the AED.

13. The defibrillator of claim 10 wherein functions d, f and j are implemented using an audible voice prompt.

14. The defibrillator of claim 10 wherein functions d, f and j are implemented using a visual prompt.

15. An automated external defibrillator (AED) having a case and a lid and a pair of electrodes wherein the AED has a processor for performing initialization and self-checking functions including:

a) monitoring a lid switch;

b) powering ON the AED when the lid switch is activated;

c) initiating a rescue mode when the lid switch is activated;

d) beginning a first analyze sequence;

e) generating a high voltage charge when a shockable rhythm is detected; and f) enabling an operator actuated button for release of a defibrillation shock.

16. The defibrillator of claim 15 wherein the rescue mode of function (c) further includes the functions of:

switching a maintenance indicator to a maintenance required stage; and flashing a rescue light.

17. The defibrillator of claim 15 wherein the lid open self-test of function (d) further includes the functions of:

checking the charge state of batteries of the AED;

checking the interconnection and operability of the electrodes;

checking the state of a memory in the AED;

checking the functionality of a real time clock of the AED; and checking the functionality of an analog to digital converter of the AED.

18. The defibrillator of claim 15 wherein functions d, f and j are implemented using an audible voice prompt.

19. The defibrillator of claim 15 wherein functions d, f and j are implemented using a visual prompt.

* * * * *

UNITED STATES PATENT AND TRADEMARK OFFICE
CERTIFICATE OF CORRECTION

PATENT NO. : 5,797,969
DATED : August 25, 1998
INVENTOR(S) : Olson, et al.

It is certified that error appears in the above-identified patent and that said Letters Patent is hereby corrected as shown below:

Column 9, line 17, after "stage;" add --and--.

Column 9, line 18, delete "and".

Column 10, line 4, after "10" add --wherein prior to the function (d) of monitoring the impedance, the processor further includes the function (h) of initiating a lid opened self-test when the lid switch is activated,--.

Column 10, line 5, after "self-test" delete "of function (d)".

Column 10, lines 14-15, after "functions" replace "d, f, and j" with --d and g--.

Column 10, lines 16-17, after "functions" replace "d, f, and j" with --d and g--.

Column 10, line 37, after "15" add --wherein prior to function (d) of beginning a first analyze sequence, the processor further includes the function (g) of initiating a lid opened self-test when the lid switch is activated,--.

UNITED STATES PATENT AND TRADEMARK OFFICE
CERTIFICATE OF CORRECTION

PATENT NO. : 5,797,969
DATED : August 25, 1998
INVENTOR(S) : Olson, et al.

It is certified that error appears in the above-identified patent and that said Letters Patent is hereby corrected as shown below:

Column 10, line 38, after "self-test" delete "of function (d)".

Column 10, lines 47 and 48, after "wherein" replace "functions d, f and j are" with --function f is--.

Column 10, lines 49 and 50, after "wherein" replace "functions d, f and j are" with --function f is--.

Signed and Sealed this

Second Day of March, 1999

Attest:

Q. TODD DICKINSON

Attesting Officer

Acting Commissioner of Patents and Trademarks